(12) United States Patent
Dietrich et al.

(10) Patent No.: US 7,018,982 B2
(45) Date of Patent: *Mar. 28, 2006

(54) METHODS USEFUL IN THE TREATMENT OF BONE RESORPTION DISEASES

(75) Inventors: John Dietrich, Ontario (CA); Sverker Ljunghall, Molndal (SE); Sven Sjögren, Molndal (SE)

(73) Assignee: NPS Allelix Corp., Toronto (CA)

( * ) Notice: Subject to any disclaimer, the term of this patent is extended or adjusted under 35 U.S.C. 154(b) by 0 days.

This patent is subject to a terminal disclaimer.

(21) Appl. No.: 10/389,797

(22) Filed: Mar. 18, 2003

(65) Prior Publication Data

US 2003/0162716 A1    Aug. 28, 2003

Related U.S. Application Data

(60) Division of application No. 09/942,661, filed on Aug. 31, 2001, now abandoned, which is a continuation of application No. 09/125,247, filed as application No. PCT/SE98/01095 on Jun. 8, 1998, now Pat. No. 6,284,730.

(30) Foreign Application Priority Data

Jun. 19, 1997   (SE) ..................... 9702401

(51) Int. Cl.
   *A61K 38/00*   (2006.01)
   *A61K 38/16*   (2006.01)

(52) U.S. Cl. ............................ 514/12; 514/8; 514/102; 514/107; 514/108; 514/808; 424/601; 424/602; 424/632

(58) Field of Classification Search .................. 514/12, 514/8, 102, 107, 108, 808; 424/601, 602, 424/632
See application file for complete search history.

(56) References Cited

U.S. PATENT DOCUMENTS

| 3,768,177 | A | 10/1973 | Thomas |
|---|---|---|---|
| 3,886,132 | A | 5/1975 | Brewer |
| 4,016,314 | A | 4/1977 | Cowans |
| 4,105,602 | A | 8/1978 | Colescott |
| 4,199,060 | A | 4/1980 | Howard |
| 4,237,224 | A | 12/1980 | Cohen |
| 4,264,731 | A | 4/1981 | Shine |
| 4,338,397 | A | 7/1982 | Gilbert |
| 4,366,246 | A | 12/1982 | Riggs |
| 4,394,443 | A | 7/1983 | Weissman |
| 4,424,278 | A | 1/1984 | Bucovaz |
| 4,425,437 | A | 1/1984 | Riggs |
| 4,468,464 | A | 8/1984 | Cohen |
| 4,532,207 | A | 7/1985 | Brewer |
| 4,546,082 | A | 10/1985 | Kurjan |
| 4,588,684 | A | 5/1986 | Brake |
| 4,595,658 | A | 6/1986 | Zinder |
| 4,624,926 | A | 11/1986 | Inouye |
| 4,690,952 | A | 9/1987 | Kagatani |
| 4,698,328 | A | * 10/1987 | Neer et al. ..................... 514/12 |
| 4,812,311 | A | 3/1989 | Uchtman |
| 4,822,609 | A | 4/1989 | Flora |
| 4,833,125 | A | 5/1989 | Neer |
| 4,904,584 | A | 2/1990 | Shaw |
| 4,994,559 | A | 2/1991 | Moscatelli |
| 5,010,010 | A | 4/1991 | Gautvik |
| 5,059,587 | A | 10/1991 | Yamamoto |
| 5,118,667 | A | 6/1992 | Adams et al. |
| 5,164,368 | A | * 11/1992 | Recker ..................... 514/12 |
| 5,171,670 | A | 12/1992 | Kronenberg |
| 5,223,407 | A | 6/1993 | Wong |
| 5,510,370 | A | 4/1996 | Hock |
| 5,550,134 | A | 8/1996 | Audia et al. |
| 5,599,822 | A | 2/1997 | Cullinan et al. |
| 5,670,514 | A | 9/1997 | Audia et al. |
| 5,861,438 | A | 1/1999 | MacLean et al. |
| 5,945,412 | A | 8/1999 | Fuh et al. |
| 6,146,852 | A | 11/2000 | Gautvik |
| 6,284,730 | B1 | * 9/2001 | Dietrich et al. ............... 514/12 |
| RE37,919 | E | 12/2002 | Kronenberg |

FOREIGN PATENT DOCUMENTS

| EP | 0123544 A2 | 10/1984 |
|---|---|---|
| EP | 0038183 B1 | 7/1985 |
| EP | 0140864 B1 | 3/1990 |
| EP | 0357391 B1 | 3/1990 |
| EP | 0163406 B1 | 1/1991 |
| EP | 0139076 B1 | 7/1992 |
| EP | 0177343 B1 | 7/1992 |
| EP | 0302772 B1 | 9/1992 |
| EP | 0792639 A1 | 9/1997 |
| EP | 0792639 A1 | 9/1997 |
| GB | 2092596 A | 8/1982 |
| GB | 2094833 A | 9/1982 |
| GB | 2248550 A | 4/1992 |
| WO | WO 83/01361 | 4/1983 |
| WO | WO 84/01173 | 3/1984 |

(Continued)

OTHER PUBLICATIONS

Dempster et al., "Anabolic Actions of Parathyroid Hormone on Bone," *Endocrine Reviews*, Baltimore, MD, US, vol. 14, No. 6, Dec. 1, 1993, pp. 690-709, XP002056317.

(Continued)

*Primary Examiner*—Christopher S. F. Low
*Assistant Examiner*—Amy Lewis
(74) *Attorney, Agent, or Firm*—Foley & Lardner LLP

(57) ABSTRACT

The invention relates to a combined pharmaceutical preparation comprising parathyroid hormone and a bone resorption inhibitor, said preparation being adapted for (a) the administration of parathyroid hormone during a period of approximately 6 to 24 months; (b) after the administration of parathyroid hormone has been terminated, the administration of a bone resorption inhibitor during a period of approximately 12 to 36 months.

16 Claims, No Drawings

FOREIGN PATENT DOCUMENTS

| WO | WO 86/03519 | 6/1986 |
| --- | --- | --- |
| WO | WO 88/00206 | 1/1988 |
| WO | WO 88/03171 | 5/1988 |
| WO | WO 89/041173 | 5/1989 |
| WO | WO 90/09167 | 8/1990 |
| WO | WO 91/06564 | 5/1991 |
| WO | WO 92/09304 | 6/1992 |
| WO | WO 93/11785 | 6/1993 |
| WO | WO 93/11786 | 6/1993 |
| WO | WO 94/08613 | 4/1994 |
| WO | WO 96/07416 A1 | 3/1996 |
| WO | WO 96/07417 | 3/1996 |
| WO | WO 96/07417 A1 | 3/1996 |
| WO | WO 97/31640 | 9/1997 |
| WO | WO 97 31640 | 9/1997 |

OTHER PUBLICATIONS

Whitfield et al., "Small bone-building fragments of parathyroid hormone: new therapeutic agents for osteoporosis," *Trends in Pharmacological Sciences*, Elsevier Trends Journal, Cambridge, GB, Nov. 1995, pp. 382-386, XP004207554.

Whitfield et al., "Comparison of the ability of recombinant human parathyroid hormone, rhPTH-(1-84), and hPTH-(1-31)NH2 to stimulate femoral trabecular bone growth in ovariectomized rats," *Calcified Tissue International*, New York, NY, US, Jan. 1, 1997, pp. 26-29, XP002249487.

Abstracts, ASBMR-IBMS, Second Joint Meeting, pp. S175, articles 1109-1112.

ASBMR 22nd Annual Meeting, Received Fax: Jan. 26, 2004, 2:39PM, Fax Station: NPS Pharmaceuticals, p. 1; SU456-SU459, p. S442.

** Bagdasarian et al, "Activity of the Hybrid trp-lac(tac) Promoter of *Escherichia coli* in Pseudomonas Putida. Construction of Broad-Host-Range, Controlled-Expression Vectors", Gene, vol. 26:273-282, (1983).

** Bell et al, "Human Epidermal Growth Factor Precursor: cDNA Sequence, Expression in Vitro and Gene Organization", Nucleic Acids Research, vol. 14:8427-8446, (1986).

Bittner et al, "Versatile Cloning Vectors Derived From The Runaway-Replication Plasmid pKN402", Gene 15: 319-329 (1981).

Black, et al., Defining Incident Vertebral Deformity: A Prospective Comparison of Several Approaches, Journal of Bone and Mineral Research, 1999, pp. 90-101, vol. 14 No. 1, Blackwell Science, Inc., USA.

** Blight et al, TIB Tech 12: 450 (1994).

** Born et al., "Expression and Processing of Human Preproparathyroid Hormone in *Escherichia coli,*" Experientia, vol. 39, 1983, p. 659.

** Born et al., (Abstract) "Expression of Human Preproathyroid Hormone in *E. coli* and Yeast," Calcified Tissue International, vol. 36, (Suppl. 2), 1984, 287.

** Born et al., (Abstract) "Expression of Human Preproparathyoid Hormone in *E. coli* and Yeast," Calcified Tissue International, vol. 35, 1983, p. 679.

Born et al., "Signal Sequence Of Human Preproparathyoid Hormone Is Inactive In Yeast", Journal Of Bone and Mineral Research, vol. 2, No. 4, p. 353-360, 1987.

** Brake et al., Alpha-Factor-directed synthesis and secretion of mature foreign proteins in *Saccharomyces cerevisiae*, Mar. 28, 1984.

Breyel et al., "Synthesis of mature human parathyroid hormone in *Escherichia coli,*" Third European Congress on Biotechnology, vol. 3, 1984, p. 363-369.

** Breyel et al., (Abstract) "Synthesis of Mature Human Parathyroid Hormone in *Escherichia Coli,*" Calcified Tissue international, vol. 36 (Suppl. 2), 1984, 297.

Brown, Homeostatic Mechanisms Regulating Extracellular and Intracellular Calcium Metabolism, The Parathyroids, 1994, pp. 15-54, Raven Press, Ltd.

** Cantrell et al., cDNA Cloning Expression, and Activity of Human Granulocyte-Macrophage Colony-Stimulating Factor, Recombinant Lymphokines and Their Receptors, 1987, pp. 187-205.

Castelo-Branco, et al., The effect of hormone replacement therapy on postmenopausal bone loss, European Journal of Obstetrics & Gynecology and Reproductive Biology, 1992, pp. 131-136, vol. 44, Elsevier Science Publishers B.V.

Cauley et al., Estrogen Replacement Therapy and Fractures in Older Women, Ann. Intern. Med., Jan. 1, 1995, pp. 9-16, vol. 122 No. 1, PA, USA.

** Chanj et al., Chem. Abst. vol. 92, No. 175928k, 1980 "Initiation of Protein Synthesis in Bacteria at a Translational Start Coden of Mammalian cDNA Effects of Preparathyroid Nucleotide Sequence".

** Charbon et al Arch Int Pharmacodyn, 1968, 171(1):3 "Diuretic and vaxcular action of parathyroid extracts in animals and man".

Cook, et al., Measuring Quality of Life in Women with Osteoporosis, Osteoporosis International, 1997, pp. 478-487, vol. 7, European Foundation for Osteoporosis and the National Osteoporosis Foundation.

Cooper, et al., Epidemiology of osteoporosis, Osteoporosis, 1996, pp. 75-77, Elsevier Science B.V.

Cosman, et al., Parathyroid Hormone Added to Established Hormone Therapy: Effects on Vertebral Fracture and Maintenance of Bone Mass After Parathyroid Hormone Withdrawal, Journal of Bone and Mineral Research, 2001, pp. 925-931, vol. 16 No. 5, American Society for bone and Mineral Research, USA.

Cranney, et al., Osteoporosis Clinical Trials Endpoints: Candidate Variables and Clinimetric Properties, The Journal of Rheumatology, 1997, pp. 1222-1229, vol. 24 No. 6, Univ. of Ottawa, Canada.

Cranney, et al., Responsiveness of Endpoints in Osteoporosis Clinical Trials—An Update, The Journal of Rheumatology, 1999, pp. 222-228, vol. 26 No. 1, Univ. of Ottawa, Canada.

Cummings, et al., Effect of Alendronate on Risk of Fracture in Women With Low Bone Density but Without Vertebral Fractures, JAMA, Dec. 23-30, 1998, pp. 2077-2082, vol. 280 No. 24, Univ. of California, USA.

** Ernest, Efficient Secretion and Processing of Heterologous Proteins in *Saccharomyces cerevisiae* Is Medicated Solely by the Pre-Segment of .alpha.-Factor Precursor, DNA, vol. 7, No. 5, 1988, pp. 355-360.

** Esposito, Yeast Molecular Biology—Recombinant DNA, Noyes Publications, pp. 93-287, COPYRGT.1984.

Ettinger, et al., Long-Term Estrogen Replacement Therapy Prevents Bone Loss and Fractures, Annals of Internal Medicine, Mar. 1985, pp. 319-324, vol. 102 No. 3, American College of Physicians, USA.

European Consensus development conference on menopause, Human Reproductive, 1996, pp. 975-979, vol. 11 No. 5, European Society for Human Reproduction and Embryology, Switzerland.

** Fairwell et al. Biochemistry 22:2691-2697, 1983.

** Fairwell et al. CA 98: 198739 (1983).

Finkelstein, et al., Pharmacological Mechanisms of Therapeutics: Parathyroid Hormone, Principles of Bone Biology, pp. 993-1005, Academic Press, Inc.

Fitzpatrick, et al., Actions of Parathyroid Hormone, Principles of Bone Biology, pp. 339-346, Academic Press, Inc.

Fox, Developments in parathyroid hormone and related peptides as bone-formation agents, Musculoskeletal, pp. 338-344, Elsevier Science Ltd.

Genant, et al., Comparison of Semiquantitative Visual and Quantitative Morphometric Assessment of Prevalent and Incident Vertebral Fractures in Osteoporosis, Journal of Bone and Mineral Research, 1996, pp. 984-996, vol. 11 No. 7, Blackwell Science, Inc.

Genant, et al., Low-Dose Esterified Estrogen Therapy, Arch Intern Med, Dec. 8-22, 1997, pp. 2609-2615, CA, USA.

Genant, et al., Universal Standardization for Dual X-ray Absorptiometry: Patient and Phantom Cross-Calibration Results, Journal of Bone and Mineral Research, 1994, pp. 1503-1514, vol. 9 No. 10, Mary Ann Liebert, Inc., CA, USA.

Genant, et al., Vertebral Fracture Assessment Using a Semiquantitative Technique, Journal of Bone and Mineral Research, 1993, pp. 1137-1148, vol. 8 No. 9, Mary Ann Liebert, Inc., USA.

** Gonoza et al., Bio Abst. No. 64386, 1982 "Effect of Bases Contiguous to Aug. on Translation Initiation".

** Gordon et al., "Synthesis, restriction analysis, and molecular cloning of near full length DNA complementary to bovine parathyroid hormone mRNA," Nucleic Acids Research, vol. 8, 1980, pp. 5669.

** Gordon et al., (Abstract), Molecular Cloning and Structural Analysis of Near Full-Length DNA Complementary To The mRNA Coding For Bovine Parathyroid Hormone, Fed. Proc., vol. 39, No. 6, p. 947, 1980.

Grady, et al., Hormone Therapy To Prevent Disease and Prolong Life in Postmenopausal Women, Annals of Internal Medicine, Dec. 15, 1992, pp. 1016-1037, vol. 117 No. 12, Univ. of California, USA.

** Guo et al., "Leakage of Cellulomonas Fimi Cellulases From *Excherichia coli*", FEMS Microbiol. Lett., vol. 49: 279-283,(1988).

Habener, et al., Parathyroid Hormone: Biochemical Aspects of Biosynthesis, Secretion, Action, and Metabolism, Physiological Reviews, Jul. 1984, pp. 985-1053, vol. 64 No. 3, The American Physiological Society, USA.

Harris, et al., The Effects of Estrone (Ogen) on Spinal Bone Density of Postmenopausal Women Arch Intern Med, Oct. 1991, pp. 1980-1984, vol. 151, CA, USA.

** Hellerman et al., "Secretion of human parathyroid hormone from rat pituitary cells infected with a recombinant retrovirus encoding preproparathyroid hormone," Proc. Natl. Acad. Sci. USA, vol. 81, Sep. 1984, pp. 5340.

** Hendy et al, "Nucleotide Sequences of Cloned cDNAs Encoding Human Preproparathyroid Hormone", Proc. Natl. Acad. Sci. USA, vol. 78, No. 12:7365-7369, (1981).

** Hendy, (Abstract) "Cloning of Human Parathyroid Hormone mRNA and Gene," Calcified Tissue International, vol. 36, 1984, 286.

Henry, et al., A systematic review of the skeletal effects of estrogen therapy in post-menopausal women. I. An Assessment of the quality of randomized trials published between 1977 and 1995, Climacteric, 1998, pp. 92-111, vol. 1.

** Hesch et al Calcif Tissue Int, 1989, 44:176 "Increase of vertebral density of combination therapy with pulsatile 1-38hPTH and sequential addition of calcitonin nasal spray in osteoporotic patients".

** Hirano et al, "Complementary DNA for a Novel Human Interleukin (BSF-2) That Induces B Lymphocytes to Produce Immunoglobulin", Nature, vol. 324:73-76, (1986).

** Hock et al Endocrinology, 1990, 127:1804 "Anabolic effect of human synthetic parathyroid hormone-(1-34) depends on growth hormone".

** Hodsman et al Bone and Mineral, 1991, 14:67 "Bone densitometric and histomorphometric responses to sequential human parathyroid hormone (1-38) and salmon calcitonin in osteoporotic patients".

** Hodsman et al Bone Miner, 1990, 9(2):137 "Biochemical responses to sequential human parathyroid hormone (1-38) and calcitonin in osteoporotic patients".

Hogset, et al., "Expression and Characterization Of A Recombinant Human Parathyroid Hormone Secreted By *Escherichia Coli* Employing the Staphylococcal Protein A Promoter And Signal Sequence", The Journal Of Biological Chemistry.

Hogset, et al., "Expression Of Human Parathyroid Hormone In *Escherichia Coli*", Biochem. And Biophysical Research Communications, vol. 156, p. 50-60, 1990.

** Hsiung et al, "High-Level Expression, Effecient Secretion and Folding of Human Growth Hormone in *Excherichia coli*", Biotechnology, vol. 4:991-995, (1986).

** Hulter et al J Clin Hypertens, 1986, 2(4):360 "Chronic continuous PTH infusion results in hypertension in normal subjects".

**Hulter et al Metabolism, 1984, 33(7):662 "Renal and systemic magnesium metabolism during chronic continuous PTH infusion in normal subjects".

** Isaac et al Horm Metab Res, 1980, 12(9):487 "Absence of effect of 1-34 hPTH on plasma TSH, GH, FSH. LH, ACTH and cortisol in normal man".

** Isaac et al J Chin Endocrinol and Metab, 1978, 47:18 "Effect of parathyroid hormone on plasma prolactin in man".

** Kabayashi et al, "Excretion of the Penicillinase of an Alkalophilic Bacillus sp. Through the *Excherichia coli* Outer Membrane is Caused By Insertional Activation of the Kil Gee in Plasmid pMB9", J. Bacteriol., 728-732,(1986).

Kanis, et al., Evidence for efficacy of drugs affecting bone metabolism in preventing hip fracture, BMJ, Nov. 7, 1992, pp. 1124-1127, vol. 305.

Kareem et al., "A Method For The Evaluation Of The Efficiency Of Signal Sequences For Secretion and Correct N-Terminal Processing Of Human Parathyroid Hormone Produced In *Escherichia Coli*", Ana. Biochem., vol. 204, p. 26-33, 1992.

Kessenich, et al., Health-Related Quality of Life and Participation in Osteoporosis Clinical Trials, Calcified Tissue International, 1998, vol. 62, pp. 189-192, Springer-Verlag New York Inc., USA.

** Keutman et al Current Research on Calcium Regulating Hormones, Cooper, C. W. (ed.), 1987, University of Texas Press, Austin, pp. 57-63.

** Keutmann et al. Biochemistry 13(8) 1646-1652, 1974.

Keutmann et al., "Complete Amino Acid Sequence of Human Parathyroid Hormone," Human Parathyroid Hormone Sequence, vol. 17, No. 26 (1978) pp. 5723-5729.

** Kimmel et al Endocrinology, 1993, 32(4):1577 "The Effect of recombinant human (1-84) or synthetic human (1-34) parathyroid hormone on the skeleton of adult osteopenic ovariectomized rats".

** Kimura et al., "Solution synthesis of [Asn.sup.76]-human parathyroid hormone (1-84)", Biochem Biophys Res Comm, 114(2):493-499, 1983.

** Koj et al, "A simple Bioassay for Monocyte-Derived Hepatocyte Stimulating Factor: Increased Synthesis of a.sub.2 -Macroglobulin and Reduced Synthesis of Albumin by Cultured Rat Hepatocytes", J. Immunol., vol. 76:317-327, (1986).

** Kronenberg et al., "Cloning and nucleotide sequence of DNA coding for bovine preproparathyroid hormone," Proc. Natl. Acad. Sci. USA, vol. 76, No. 10, Oct. 1979, pp. 4981.

** Kronenberg et al., "Studies of Parathyroid Hormone Secretion Using Recombinant DNA Technology," Endocrine control of bone and calcium metabolism, vol. 8A, 1994, pp. 217-220.

** Kronenberg et al., (Abstract), "Structural Analysis of the Human Parathyroid Hormone Gene," Calcified Tissue International, vol. 33, 1981, p. 322.

** Kumagaye et al., J. Chromatography 327:327-332, 1985.

Kunkel, "Rapid And Efficient Site-Specific Mutagenesis Without Phenotypic Selection", Proc. Natl. Acad. Sci. USA, vol. 82:488-492, (1985).

Lacey, Jr., et al., Menopausal Hormone Replacement Therapy and Risk of Ovarian Cancer, JAMA, Jul. 17, 2002, pp. 334-341, vol. 288 No. 3, American Medical Association, USA.

** Law et al J Clin Invest, 1983, 72(3):1106 "Rapid development of renal resistance to low doses of synthetic bovine parathyroid hormone fragement 1-34".

** Lawoyin et al J Clin Endocrinol Metab, 1979, 49:783 "A patient with pseudohypoparathyroidism with increased serum calcium and 1.alpha.,25-dihydroxyvitamin D after exogenous parathyroid hormone administration".

** Lee, "Peptide and Protein Drug Delivery", published by Marcel Dekker, Inc., (N.Y.), pp. 514-516 and 538.

** Leithner et al The Lancet, 1984, :367 "Parathyroid hormone does not inhibit platelet aggregation".

Lindsay, et al., The Minimum Effective Dose of Estrogen for Prevention of Postmenopausal Bone Loss, Journal of The American College of Obstetricians and Gynecologists, Jun. 1984, vol. 63 No. 6, Helen Hayes Hospital, NY, USA.

Looker, et al., Prevalence of Low Femoral Bone Density In Older U.S. Women From NHANES III, Journal of Bone and Mineral Research, 1995, pp. 796-802, vol. 10 No. 5, Blackwell Science, Inc.

** Mackman et al, "Release of a Chimeric Protein Into the Medium From Escherichia coli Using the C-Terminal Secretion Signal of Haemolysin", EMBO J., vol. 6:2835-2841, (1987).

** Maddon et al, "The Isolation and Nucleotide Sequence of a cDNA Encoding the T Cell Surface Protein T4: A New Member of the Immunoglobulin Gene Family", Cell, vol. 42:93-104, (1985).

** Martindale The Extra Pharmacoepia, The Pharmaceutical Press, London, 29th ed., 1989 at p. 1338 "Parathyroid calcitonin and biphosphonates".

Maxim, et al., Fracture Protection Provided by Long-Term Estrogen Treatment, Osteoporosis International, 1995, pp. 23-29, vol. 5, European Foundation for Osteoporosis.

** McDevitt et al., (Abstract) "Isolation of Human Parathyroid Hormone Genes," Calcified Tissue International, vol. 31, 1980, p. 74.

Michaëlsson et al., hormone replacement therapy and risk of hip fracture: population based case-control study, BMJ, Jun. 20, 1998, pp. 1858-1863, vol. 316.

Michaëlsson, et al., Diet and Hip Fracture Risk: A Case-Control Study, International Journal of Epidemiology, pp. 771-782, vol. 24 No. 4, International Epidemiological Association, GB.

** Miller et al, "Nucleotide Sequence of the Partition Locus of Escherichia coli Plasmid pSC101", Gene, vol. 24:309-315, (1983).

Naessén, et al., Hormone Replacement Therapy and the Risk for First Hip Fracture, A Prospective, Population-based Cohort Study, Annals of Internal Medicine, Jul. 15, 1990, pp. 95-103, vol. 113 No. 2, American College of Physicians, USA.

** Nagahari et al, "Secretion Into the Culture Medium of a Foreign Gene Product From Escherichia coli: Use of the ompF Gene For Secretion of Human B-Endorphin", EMBO J., vol. 4:3589-3592, (1985).

** Naylor et al., "Human Parathyroid Hormone Gene (PTH) Is on Short Arm of Chromosome 11," Somatic Cell Genetics, vol. 9, No. 5, 1983, pp. 609-616.

Neer, et al., Effect of parathyroid hormone (1-34) on fractures and bone mineral density in postmenopausal women with osteoporosis, N Engl J Med, May 10, 2001, pp. 1434-1441, vol. 344 No. 19 [downloaded from www.nejm.org at NPS Pharmaceuticals on Jan. 26, 2004].

Niall et al., "the Amino-Acid Sequence Of the Amino-Terminal 37 Residues Of Human Parathyroid Hormone", Proc. Nat. Acad. Sci. USA 71(2):384-388, Feb. 1974.

** Nossal et al, "The Releae of Enzymes by Osmotic Shock From Escherichia coli in Exponential Phase", J. Biol. Chem., vol. 241:3055-3062, (1966).

O'Brien et al., A Multiple Testing Procedure for Clinical Trials, Biometrics, Sep. 1979, pp. 549-556, vol. 35, Minnesota, USA.

O'Brien, Procedures for Comparing Samples with Multiple Endpoints, Biometrics, Dec. 1984, pp. 1079-1087, vol. 40, Minnesota, USA.

** Oka et al, "Synthesis and Secretion of Human Epidermal Growth Factor by Escherichia coli", Proc. Natl. Acad. Sci. USA, vol. 82:7212-7216 (1985).

** Old et al., "Principles of Gene Manipulation, an Introduction to Genetic Engineering", Blackwell Scientific Publications, 3rd ed.,. pp. 183-202, .COPYRGT.1985.

Olstad et al., "Expression and Characterization Of A Recombinant Human Parathyroid Hormone Partial Agonist With Antagonistic Properties: Gly-hPTH(1→+84)", PEPTIDES, vol. 16, No. 6, p. 1031-1037, 1995.

Parfitt et al., Bone Histomorphometry: Standardization of Nomenclature, Symbols, and Units, Journal of Bone and Mineral Research, 1987, pp. 595-610, vol. 2 No. 6, Mary Ann Liebert, Inc., USA.

** Rabbani et al Endocrinology, 1988, 123:2709 "Influence of the amino-terminus on in vitro and in vivo biological activity of synthetic parathyroid hormone-like peptides of malignancy".

Rabbani et al, "Recombinant Human Parathyroid Hormone Synthesized In Escherichia coli, The Journal of Biological Chemistry", vol. 263:1307-1313, (1988).

** Rabbani et al. CA 109:5186 (1988).

** Reeve et al Br Med J, 1980, 280:1340 "Anabolic effect of human parathyroid hormone fragment on trabecular bone in involutional osteoporosis: a multicentre trial".

** Reeve et al Calcif Tissue Res, 1976, 21:469 "Preliminary trial of low doses of human parathyroid hormone peptide in treatment of osteoporosis".

** Reeve et al Lancet, 1976, 1:1035 "Anabolic effect of low doses of a fragment of human parathyroid hormone on the skeleton in postmenopausal osteoporosis".

** Reeve et al Osteoporosis Int, 1991, 1:162 "hPTH 1-34 treatment of osteoporosis with added hormone replacement therapy: biochemical, kinetic and histological responses".

Riggs, et al., Effect of the fluoride/calcium regimen on vertebral fracture occurrence in postmenopausal osteoporosis, N Engl J Med, Feb. 25, 1982, pp. 446-450, vol. 306 No. 8, Mayo Foundation, Minn., USA.

** Rodan et al J Clin Invest, 1983, 72:1511 "Factors associated with humoral hypercalcemia of malignancy stimulate adenylate cyclase in osteoblastic cells".

** Rosenberg et al, "Regulatory Sequences Involved in the Promotion and Termination of RNA Transcription", Ann. Rev. Genet., vol. 13:319-353, (1979).

Rossouw, et al., Risks and Benefits of Estrogen Plus Progestin in Healthy Postmenopausal Women, Principal Results From the Women's Health Initiative Randomized Controlled Trial, JAMA, Jul. 17, 2002, pp. 321-333, vol. 288 No. 3, American Medical Association, USA.

Schneider, et al., Timing of Postmenopausal Estrogen for Optimal Bone Mineral Density, JAMA, Feb. 19, 1997, pp. 543-547, vol. 277 No. 7, Univ. of California, USA.

Schwietert, et al., Clinical Trials and Therapeutics, Single-dose subcutaneous administration of recombinant human parathyroid hormone [rhPTH(1-84)] in healthy postmenopausal volunteers, Clinical Pharmacology & Therapeutics, Mar. 1997, pp. 360-376, Pharma Bio-Research International BV, The Netherlands.

Silver, et al., Parathyroid Hormone—Molecular Biology and Regulation, Principles of Bone Biology, pp. 325-337, Academic Press, Inc.

** Slovik et al J Bone and Mineral Res, "Restoration of spinal bone in osteoporotic men by treatment with human parathyroid hormone (1-34) and 1,25-dihydroxyvitamin D", 1986, 1(4):377.

Slovik, et al., Renal 1,25-Dihydroxyvitamin D, Phosphaturic, and Cyclic-AMP Responses to Intravenous Synthetic Human Parathyroid Hormond-(1-34) Administration in Normal Subjects, Clinical Endocrinology, 1984, pp. 369-375, vol. 20.

** Sofer et al., Bio Techniques, Nov./Dec. 1983, pp. 198-203.

Stevenson, et al., Effects of Parathyroid Hormone and the Synthetic 1-34 Amino-terminal Fragment in Rats and Dogs, Journal of Endocrinology, Ltd., 1983, pp. 21-30, vol. 97, Great Britain.

Stevenson, et al., Effects of transdermal versus oral hormone replacement therapy on bone density in spine and proximal femur in postmenopausal women, The Lancet, Aug. 4, 1990, pp. 265-269, vol. 336.

Stevenson, et al., Hormone replacement therapy, Findings of women's health initiative trial need not alarm users, BMJ, Jul. 20, 2002, pp. 113-114, vol. 325.

Sung et al., "Hybrid gene synthesis: its application to the assembly of DNA sequences encoding the human parathyroid hormones and analogues," Biochem. Cell Biol., vol. 64, No. 2, 1986, pp. 133-138.

** Sung, et al, "Specific Degenerate Codons Enhanced Selective Expression Of Human Parathyroid Hormone in *Escherichia Coli*", The Journal of Biological Chemistry, vol. 266, pp. 2831-2835, (1991).

Tam, et al., Parathyroid Hormone Stimulates the Bone Apposition Rate Independently of Its Resorptive Action: Differential Effects of Intermittent and Continuous Administration, Endocrinology, 1982, pp. 506-512, vol. 110 No. 2, The Endocrine Society, USA.

Torgerson, et al., Hormone Replacement Therapy and Prevention of Nonvertebral Fractures, A Meta-analysis of Randomized Trials, JAMA, Jun. 13, 2001, pp. 2891-2897, vol. 285 No. 22, American Medical Association, USA.

** Tsai et al J Clin Endocrinol Metab, 1989, 69(5):1024 "Bone responsiveness to parathyroid hormone in normal and osteoporotic postmenopausal women".

** Van Kimmenade et al., "Secretion Of Murine and Human Intterleukin-2 By *Escherichia coli*", Journal of Biotechnology, vol. 11:11-24, (1989).

** Vasicek et al., "Nucleotide sequence of the human parathyroid hormone gene," Proc. Natl. Acad. Sci. USA, vol. 80, No. 8, Apr. 1983, pp. 2127-2131.

Ware, Jr., et al., The MOS 36-Item Short-Form Health Survey (SF-36), Medical Care, Jun. 1992, pp. 473-483, vol. 30 No. 6.

** Watson, "Compilation of Published Signal Sequences", Nucleic Acids Research, vol. 12:5145-5164, (1984).

** Watson, James D., Tooze, John and Kurtz, David T., Recombinant DNA, A Short Course, Scientific American Books, pp. 2-16, New York, .COPYRGT. 1983.

** Wong et al, "Wood Hydrolysis by Cellulomonas Fimi Endoglucanase and Exoglucanase Coexpressed as Secreted Enzymes in Saccharomyces Cerevisiae", Bio/Tecnology, vol. 6:713-719, (1988).

** Wosnick et al, "Rapid Construction of Large Synthetic Genes: Total Chemical Synthesis of Two Different Versions of the Bovine Prochymosin Gene," Gene, vol. 60:115-127, (1987).

* cited by examiner

METHODS USEFUL IN THE TREATMENT OF BONE RESORPTION DISEASES

This is a divisional application of application Ser. No. 09/942,661, filed Aug. 31, 2001, now abandoned, which is a continuation of Ser. No. 09/125,247, filed Aug. 14, 1998, now U.S. Pat. No. 6,284,730, which is a 371 of PCT/SE98/01095, filed Jun. 8, 1998, based on Swedish application No. 9702401-2, filed Jun. 19, 1997.

TECHNICAL FIELD

The present invention relates to a combined pharmaceutical preparation comprising parathyroid hormone and a bone resorption inhibitor, for sequential use in the treatment of bone-related diseases.

BACKGROUND ART

Bone Formation and Resorption

In the adult individual (males as well as females) bone is continuously subject to remodeling. This is a process where bone resorption is closely linked to bone formation, through the concerted action of the bone active cells, i.e. the bone forming osteoblasts and the bone resorbing osteoclasts. These cells together form what is called a basal multicellular (metabolic) unit, or BMU. The remodeling process starts with activation of the lining cells (the cells that cover the unmineralized bone). The lining cells resorb the unmineralized bone, then retract and leave room for the osteoclasts which resorb the old, mineralized bone and create an environment which attracts the osteoblast to the same site. The osteoblasts thereafter lay down the organic matrix, which subsequently is becoming mineralized to form new bone. The resulting bone mass is thus determined by the balance between resorption by osteoclasts and formation by osteoblasts.

Consequently, there is a close relationship between the actions of the two cell types which is referred to as "coupling"; bone resorption always precedes bone formation. The coupling phenomenon means that even when the intention is to produce a positive balance per cycle it is still necessary to start with bone resorption. Typically, a BMU cycle takes 3 to 6 months to complete.

The rate by which the basal metabolic (multicellular) units are being activated, the activation frequency, also plays a role. A high activation frequency increases the rate by which bone is being lost if there is a negative balance per remodeling cycle. When activation frequency is increased the space that is being occupied by remodeling, the remodeling space, is also increased. This will give a lowered bone mass, since a greater portion of the bone is subject to resorption as part of the remodeling process.

The above outlined sequence of events is well known in the art and has formed the basis for the understanding of metabolic bone diseases and possible ways for their treatments.

Osteoporosis is a disease which is characterized by a reduced amount of bone tissue, usually of normal composition, which has reduced strength due to a combination of low bone mass and impaired architecture, and therefore carries an increased risk of fractures. In terms of remodeling, osteoporosis is the result of negative bone balance per remodeling cycle, i.e. less bone is formed than is being resorbed. In a small proportion of patients it is possible to determine a specific disease as responsible for the loss of bone (e.g. malabsorption of calcium and hypersecretion of corticosteroid hormones) but in the majority of patients no such disorder is identified. Such patients are classified as having "primary" osteoporosis. Bone is lost with advancing age in both sexes, but in females there is generally an increased rate of loss during the first years after the menopause (hence the term "postmenopausal" osteoporosis).

Bone Resorption Inhibitors

A number of agents have been used for the prevention and treatment of bone loss and osteoporosis, e.g. estrogen, vitamin D and bisphosphonates, such as alendronate (for a review, see: Osteoporosis (Marcus, R., Feldman, D. and Kelsey, F., Eds.) Academic Press, San Diego, 1996). Such agents mainly act through inhibition of bone resorption. By reducing the resorbed amount in each remodeling cycle, while keeping the formation intact, it is possible to reduce the negative bone balance and retard bone loss. At the same time they reduce the activation frequency and since the remodeling space is reduced there is only a limited increase of bone mass.

Most studies with bisphosphonates indicate that they increase bone mineral density of the lumbar spine in the actively treated patients with around 1 to 5%, depending on dose and type of bisphosphonate, during the first year of treatment, when compared with control patients given placebo. Both patients and controls generally receive calcium supplementation to ensure adequate calcium nutrition.

The antiresorptive agents can retard bone loss but, by definition, they do not increase bone mass within each remodeling unit. Many patients with fractures have severe bone loss at the time they come to clinical attention. Inhibition of bone resorption might not be enough to prevent fracture recurrences. Therefore it is urgent to develop therapies that can increase bone mass, i.e. anabolic agents.

Parathyroid Hormone

Parathyroid hormone (PTH) is an 84 amino acid polypeptide which is normally secreted from the parathyroid glands. PTH has an important physiological role to maintain serum calcium within a narrow range. Furthermore, it has anabolic properties when given intermittently. This has been well documented in a number of animal and open clinical studies, recently reviewed by Dempster, D. W. et al. (Endocrine Reviews 1993, vol. 14, 690–709). PTH has a multitude of effects on bone. Part of it is through the remodeling cycle. PTH causes both increased activation frequency and a positive balance per cycle.

Human PTH may be obtained through peptide synthesis or from genetically engineered yeast, bacterial or mammalian cell hosts. Synthetic human PTH is commercially available from Bachem Inc., Bubendorf, Switzerland. Production of recombinant human parathyroid hormone is disclosed in e.g. EP-B-0383751.

PTH when given alone, to a patient with osteoporosis, will stimulate bone formation within each remodeling cycle and cause a positive bone balance within each cycle. At the same time the number of remodeling units will greatly increase, i.e. the activation frequency is enhanced. These two mechanisms act in different directions on bone mass.

During therapy with PTH it has been calculated that the activation frequency is doubled. Although this will mean that the remodeling space is increased, bone mass (or bone density) is increased in trabecular bone. Thus bone mineral density is increased by 5 to 10% per year in the lumbar spine and is largely unaffected in the femoral neck, which contains a higher proportion of cortical bone. These two sites are where the most common and clinically important fractures occur in the population, both in males and females.

The presently known methods for treatment of osteoporosis utilize bone resorption inhibition of the BMU cycle, but have the drawbacks that their onset of effect is slow and limited, and that they only cause moderate increases of bone mineral density (bone mass) and may therefore be insufficient for the treatment of patients with osteoporosis in a stage where there is high risk of recurrent fractures. Furthermore, it has not been shown that present methods can improve on the altered architecture that is a hallmark of advanced osteoporosis.

A method of treatment of bone metabolism disorders, utilizing the order of events in the BMU cycle, and comprising administering a bone active phosphonate and, sequentially, parathyroid hormone, is disclosed in WO 96/07417 (The Procter & Gamble Company). In that method, the bone active phosphonate is given for a period of greater than about 6 months, in various dosage regimens, but always prior to PTH.

Hodsman, A. et al. (J. Bone and Mineral Research, Vol. 10, Suppl. 1, abstract No. P288, p. S200, 1995) discloses a clinical trial involving treatment with PTH for 28 days, with our without sequential calcitonin for 42 days, with this cycle repeated at 3 months intervals for 2 years. Patients were then crossed over to clodronate, 28 days per 3 months, for one year. However, there was no beneficial effect in bone density from this sequential PTH/bisphosphonate treatment regimen.

WO 97/31640 (publication date 4 Sep. 1997) discloses a pharmaceutical composition comprising (a) an estrogen agonist/antagonist; and (b) a bone activating compound, such as parathyroid hormone. However, the periods of treatment are broadly defined and it is stated that the said compounds can be administered for periods from about three months to about three years.

DISCLOSURE OF THE INVENTION

Different combinations are conceivable for treating osteoporosis with resorption inhibitors and anabolic agents. The starting point for treatment, i.e. when the patient comes to the attention of the clinic, is a decreasing BMD (bone mineral density), due to the net formation rate being below the net resorption rate. Initial administration of a resorption inhibitor will reduce resorption rate by reducing the remodeling space and the activation frequency. Subsequent administration of an anabolic agent will then increase activation frequency and create an increased remodeling space. This coupling between resorption and reformation allows the formation rate to increase above the resorption rate and lead to increases in BMD. The resorption activity is a prerequisite for subsequent bone formation within the BMU.

However, it has surprisingly been found that when the anabolic agent was administered initially, i.e. as the starting point, and is then followed by administration of the resorption inhibitor, the total increase in BMD is not only maintained but also much further increased. It appears that the initial increase in activation frequency by the anabolic agent creates not only formation of new bone, but also a large remodeling space. Subsequent administration by the resorption inhibitor, inhibits further increases in the remodeling space, by decreasing the activation frequency. Upon closing, or diminishing, the existing remodeling space, BMD is then allowed to increase more than was achieved during treatment with the anabolic agent alone during the first period.

The present invention is thus based on the concept of remodeling. By overriding the resorptive phase of the BMU over several consecutive cycles, it fortifies the anabolic action of PTH. In addition, by prolonging the treatment over several BMU cycles, it takes advantage of the opposite influences on the activation frequency which is increased by PTH and later reduced by bisphosphonates.

As mentioned above, WO 96/07417 discloses a method of treatment of bone metabolism disorders, comprising administering a bone active phosphonate and, subsequently, parathyroid hormone. The bone active phosphonate was thus given prior to PTH. The order of treatment regimens provides principally different treatment responses. Slowing down the remodeling cycle with a resorption inhibitor would limit the maximum anabolic effect that can be obtained with PTH. On the other hand, if PTH is given first over several BMU cycles, not only will it enhance the BMU positive bone balance significantly, it will also increase activation frequency to such an extent that effects of subsequent antiresorptive therapy will be enhanced.

According to the present invention, a bisphosphonate is given after PTH treatment, in order not only to maintain bone mass on the higher level by its antiresorptive action, but also to increase BMD by filling in the increased remodeling space through the reduction of activation frequency.

A BMU cycle, involving activation, resorption, formation, typically takes 3 to 6 months to complete. The number of BMU cycles acting concurrently determines the remodeling space. In order to create an increased and sustained remodeling space, treatment with an agent that increases the activation frequency must be of sufficient duration, i.e. it must cover several BMU cycles (e.g. 6 to 12 months). Only then can the full potential of the treatment, with regards to increases in BMD, develop.

It has thus surprisingly been found that the method of treatment according to the invention achieves the advantageous result that bone mass is first rapidly increased during PTH treatment and thereafter further bone mineral density is gained, compared to the results achieved with bisphosphonates alone without prior activation by PTH. These findings are in contrast to previous studies in humans.

Consequently, the present invention provides in a first aspect a combined pharmaceutical preparation comprising parathyroid hormone and a bone resorption inhibitor, said preparation being adapted for (a) the administration of parathyroid hormone during a period of approximately 6 to 24 months, preferably about 12 (or above 12) months to 24 months or about 12 (or above 12) months to 18 months, or more preferably about 18 months; and (b) after the administration of said parathyroid hormone has been terminated, the administration of a bone resorption inhibitor during a period of approximately 6 to 36 months, preferably about 12 to 36 months or about 12 to 18 months, or more preferably about 12 months.

This sequence of treatments can be repeated at intervals of one to five years, until BMD has reached a value corresponding to "young normal mean". Preferably, the interval between treatments coincides with the period of one treatment cycle, i.e. 12 to 60 months, preferably 24 to 60 months or 24 to 42 months, or more preferably 30 to 36 months.

The term "parathyroid hormone" (PTH) encompasses naturally occurring human PTH, as well as synthetic or recombinant PTH (rPTH).

Further, the term "parathyroid hormone" encompasses full-length PTH(1-84) as well as PTH fragments. It will thus be understood that fragments of PTH variants, in amounts giving equivalent biological activity to PTH(1-84), can be incorporated in the formulations according to the invention, if desired. Fragments of PTH incorporate at least the amino acid residues of PTH necessary for a biological activity similar to that of intact PTH. Examples of such fragments are PTH(1-31), PTH(1-34), PTH(1-36), PTH(1-37), PTH(1-38), PTH(1-41), PTH(28-48) and PTH(25-39).

The term "parathyroid hormone" also encompasses variants and functional analogues of PTH. The present invention thus includes pharmaceutical formulations comprising such PTH variants and functional analogues, carrying modifications like substitutions, deletions, insertions, inversions or cyclisations, but nevertheless having substantially the biological activities of parathyroid hormone. Stability-enhanced variants of PTH are known in the art from e.g. WO 92/11286 and WO 93/20203. Variants of PTH can e.g. incorporate amino acid substitutions that improve PTH stability and half-life, such as the replacement of methionine residues at positions 8 and/or 18, and replacement of asparagine at position 16. Cyclized PTH analogues are disclosed in e.g. WO 98/05683.

Consequently, the invention includes a preparation as described above wherein the said parathyroid hormone is selected from the group consisting of:
(a) full-length parathyroid hormone;
(b) biologically active variants of full-length parathyroid hormone;
(c) biologically active parathyroid hormone fragments; and
(d) biologically active variants of parathyroid hormone fragments.

In this context, the term "biologically active" should be understood as eliciting a sufficient response in a bioassay for PTH activity, such as the rat osteosarcoma cell-based assay for PTH-stimulated adenylate cyclase production (see Rodan et al. (1983) J. Clin. Invest. 72, 1511; and Rabbani et al. (1988) Endocrinol. 123, 2709).

The PTH to be used in the pharmaceutical preparation according to the invention is preferably recombinant human PTH, such as full-length recombinant human PTH. Parathyroid hormone can be subcutaneously administered in an amount of approximately 0.1 to 5 µg/kg body weight, preferably 0.5 to 3 µg/kg, or more preferably 1 to 2.5 µg/kg body weight. Orally, nasally or pulmonary, PTH can be administered in an amount of 0.1 µg to 15 mg/kg.

The said bone resorption inhibitor can be a bisphosphonate, e.g. alendronate; or a substance with estrogen-like effect, e.g. estrogen; or a selective estrogen receptor modulator, e.g. raloxifene, tamoxifene, droloxifene, toremifene, idoxifene, or levormeloxifene; or a calcitonin-like substance, e.g. calcitonin; or a vitamin D analog; or a calcium salt.

The said bone resorption inhibitor is preferably administered in an amount of 0.05 to 500 mg, preferably around 10 mg.

In a further aspect, the invention provides the use of parathyroid hormone in combination with a bone resorption inhibitor in the manufacture of a medicament for the treatment or prevention of bone-related diseases, in particular osteoporosis, said medicament being adapted for (a) the administration of parathyroid hormone during a period of approximately 6 to 24 months; (b) after the administration of parathyroid hormone has been terminated, the administration of a bone resorption inhibitor during a period of approximately 12 to 36 months. The parathyroid hormone and the bone resorption inhibitor are as defined above.

In yet a further aspect, the invention provides a method of treatment or prevention of bone-related diseases, in particular osteoporosis, which comprises administering to a mammal, including man, in need of such treatment an effective amount of a pharmaceutical preparation as defined in the above. Consequently, such a method comprises administering to a mammal, including man, in need of such treatment (a) an effective amount of parathyroid hormone during a period of approximately 6 to 24 months; and (b) after the administration of parathyroid hormone has been terminated, an effective amount of a bone resorption inhibitor during a period of approximately 12 to 36 months.

The invention also includes a method of treatment or prevention of bone-related diseases which comprises administering, to a patient who has already been subject to treatment with parathyroid hormone during a period of approximately 6 to 24 months, after the administration of parathyroid hormone has been terminated, an effective amount of a bone resorption inhibitor during a period of approximately 12 to 36 months.

EXAMPLE OF THE INVENTION

Postmenopausal females (n=172) with osteoporosis were given intact human PTH (1-84), as a subcutaneous injection, for one year in doses from 50 to 100 micrograms daily. It was shown that bone mineral density of the spine was increased in the lumbar spine, on the average by 8%. Increases in individual patients were considerably more than 10%. The changes of the femoral neck were smaller and ranged from 1 to 3%.

When administration of PTH was interrupted, some patients (approximately 60) were given the bisphosphonate alendronate in a standard dose of 10 mg for one year. After the combined treatment, bone mineral density was further increased in that group of patients. The average gain in the femoral neck over the two years was 6% and of the lumbar spine 15%. Again, some individual responses were considerably larger and amounted to more than 25% in the spine.

These new observations demonstrate that it is possible to achieve an enhanced effect on bone mineral density with the sequential administration of PTH and bisphosphonates.

What is claimed is:

1. A method for enhancing bone mineral density in a human needing enhancement of bone density, consisting essentially of administering to said human a human PTH (1-84) pharmaceutical formulation, having a single active agent consisting of a human PTH (1-84), and is administered once daily at a PTH (1-84) dose of 50–100 µg.

2. The method according to claim 1, wherein said PTH (1-84) is administered for at least twelve months.

3. The method according to claim 1, wherein said human is a post-menopausal female.

4. The method according to claim 3, wherein said female is afflicted with osteoporosis.

5. The method according to claim 1, 2, 3 or 4, wherein after said PTH(1-84) treatment regimen is terminated, said human is treated with a bone resorption inhibitor.

6. The method according to claim 1, 2, 3 or 4, wherein the human PTH(1-84) is administered at a dose of 100 µg.

7. A method for treating a post menopausal female human afflicted with osteoporosis to enhance bone mineral density of said human consisting essentially of administering to said human a human PTH (1-84) pharmaceutical formulation, having a single active agent consisting of a human PTH (1-84), and is administered to said human by subcutaneous injection once daily at a PTH (1-84) dose of 100 µg for a period of 12 months.

8. The method of claim 7, wherein said human PTH(1-84) is administered for a period of from about 6 to about 12 months.

9. A method for enhancing bone mineral density in a human needing enhancement of bone density, consisting essentially of administering to said human a human PTH (1-84) pharmaceutical formulation, having a single active agent consisting of a human PTH (1-84), once daily at a PTH (1-84) dose of 50–100 μg as a monotherapy, in combination with vitamin D, in combination with calcium, or in combination with vitamin D and calcium.

10. The method according to claim 9, wherein said PTH (1-84) is administered for at least twelve months.

11. The method according to claim 9, wherein said human is a post-menopausal female.

12. The method according to claim 11, wherein said female is afflicted with osteoporosis.

13. The method according to claim 9, 10, 11 or 12, wherein after said PTH(1-84) treatment regimen is terminated, said human is treated with a bone resorption inhibitor.

14. The method according to claim 9, 10, 11 or 12, wherein the human PTH(1-84) is administered at a dose of 100 μg.

15. The method of claim 9, wherein said human PTH(1-84) is administered for a period of from about 6 to about 12 months.

16. A method for treating a post menopausal female human afflicted with osteoporosis to enhance bone mineral density of said human consisting essentially of administering to said human a human PTH (1-84) pharmaceutical formulation, having a single active agent consisting of a human PTH (1-84), by subcutaneous injection once daily at a PTH (1-84) dose of 100 μg for a period of 12 months as a monotherapy, in combination with vitamin D, in combination with calcium, or in combination with vitamin D and calcium.

* * * * *